United States Patent
Wang et al.

(10) Patent No.: US 9,596,984 B2
(45) Date of Patent: Mar. 21, 2017

(54) DEVICES AND METHODS FOR MEASURING PARAMETERS ASSOCIATED WITH ANIMAL EYE HEALTH

(71) Applicant: NESTEC SA, Vevey (CH)

(72) Inventors: Wei Wang, Creve Coeur, MO (US);
Tyler Simpson, Cuba, MO (US);
Virginia Louise Wilson, St. Louis, MO (US); Dwight Estes Howdeshell, Arnold, MO (US)

(73) Assignee: Nestec SA, Vevey (CH)

( * ) Notice: Subject to any disclaimer, the term of this patent is extended or adjusted under 35 U.S.C. 154(b) by 153 days.

(21) Appl. No.: 14/413,955

(22) PCT Filed: Jul. 12, 2013

(86) PCT No.: PCT/US2013/050193
§ 371 (c)(1),
(2) Date: Jan. 9, 2015

(87) PCT Pub. No.: WO2014/011952
PCT Pub. Date: Jan. 16, 2014

(65) Prior Publication Data
US 2015/0201830 A1    Jul. 23, 2015

Related U.S. Application Data

(60) Provisional application No. 61/671,292, filed on Jul. 13, 2012.

(51) Int. Cl.
*A61B 3/00* (2006.01)
*B65D 25/20* (2006.01)
(Continued)

(52) U.S. Cl.
CPC .......... *A61B 3/0083* (2013.01); *A61B 3/0075* (2013.01); *B65D 25/205* (2013.01);
(Continued)

(58) Field of Classification Search
CPC ........... A61B 3/14; A61B 3/103; A61B 3/107; A61B 3/10; A61B 3/18; A61B 3/1035; A61B 3/13
(Continued)

(56) References Cited

U.S. PATENT DOCUMENTS 3,594,072 A * 7/1971 Feather .................... A61B 3/00
248/118
2011/0083614 A1 4/2011 Chen et al.

FOREIGN PATENT DOCUMENTS

DE      91 16 002      2/1992
EP      1 413 243      4/2004
(Continued)

OTHER PUBLICATIONS

Kunal D Chaniary et al: "A novel stereotaxic apparatus for neuronal recordings in awake head restrained rats" Journal of Neuroscience Methods, Elsevier Science Publisher.
(Continued)

*Primary Examiner* — Hung Dang
(74) *Attorney, Agent, or Firm* — Ronald A. Burchett; Julie M. Lappin

(57) ABSTRACT

The invention provides methods and devices for securing the head of an animal in position while obtaining objective measurements associated with eye health. In one aspect, the devices comprise a rest for receiving a portion of the animal's head and a pole configured to enable the rest to pivot about a first axis of rotation and rotate about a second axis of rotation perpendicular to the first axis of rotation. In an embodiment, the rest can move up and down the second axis of rotation.

20 Claims, 4 Drawing Sheets

(51) Int. Cl.
  *B65D 25/28*  (2006.01)
  *B65D 25/54*  (2006.01)
  *B65D 85/00*  (2006.01)
  *A61G 15/12*  (2006.01)
  *A61D 3/00*   (2006.01)
  *A61G 13/12*  (2006.01)
(52) U.S. Cl.
  CPC ............ *B65D 25/28* (2013.01); *B65D 25/54* (2013.01); *B65D 85/70* (2013.01); *A61D 2003/003* (2013.01); *A61G 13/121* (2013.01); *A61G 15/125* (2013.01)
(58) Field of Classification Search
  USPC ........ 351/245, 246, 244, 222; 119/729, 730, 119/731
  See application file for complete search history.

(56) References Cited

FOREIGN PATENT DOCUMENTS

SU          908 349        2/1982
WO    WO 2007/120356      10/2007

OTHER PUBLICATIONS

BV Amsterdam, NL, vol. 198, No. 1, Feb. 28, 2011 pp. 29-35 XP028383802.
International Search Report dated Oct. 9, 2013 for PCT/US2013/050193.

* cited by examiner

DEVICES AND METHODS FOR MEASURING PARAMETERS ASSOCIATED WITH ANIMAL EYE HEALTH

CROSS REFERENCE TO RELATED APPLICATIONS

This application is a national stage application under 35 USC §371 of PCT/US2013/050193 filed on 12 Jul. 2013 and claims priority to U.S. Provisional Application No. 61/671,292 filed 13 Jul. 2012, the disclosures of which are incorporated herein by this reference.

BACKGROUND OF THE INVENTION

Field of the Invention

The invention relates generally to devices and methods for measuring parameters associated with animal eye health and particularly devices aid methods for securing an animal's eye in position while obtaining objective measurements associated with eye health.

Description of Related Art

Eyes are a critical sensory organ for both humans and animals. Therefore, although eye diseases are typically not fatal, an eye disease or disorder that weakens vision or eventually results in loss of vision can significantly impair everyday life of a human or an animal.

Various types of devices diagnose eye health by projecting light into the eye of the patient. Such eye health, measurement devices obtain light measurements regarding distortion, reflection, retraction, wavefront changes and/or the like caused by components of the eye. These light measurements are used to determine the presence or absence of eye aberrations and the location of any eye aberrations. The effectiveness and accuracy of such devices are dependent upon proper positioning of the measurement device relative to the eye, and sometimes more specifically the cornea and/or the pupil, and misalignment of the measurement device results in inaccurate measurements and potentially a misdiagnosis.

Thus, the eye being examined must have a specific position relative to the measurement device, such as a specific distance from the device, a specific height relative to the device, and specific angles relative to the device in both the vertical and horizontal planes. In addition, the eye must maintain this position continuously as the device obtains the eye health measurements.

These requirements render eye health measurement devices unusable for most animals because animals typically will not "stay still," i.e., maintain the same position for a time sufficient to measure the animal's eye. For example, even if an animal maintains its general body position for art amount of time, the animal will typically adjust the position of the head and thereby change the position of the eyes as the head moves.

Furthermore, for repeated examinations of an animal to produce measurements that can be compared, a consistent position of the animal's head and eyes in each examination is needed. Consistently positioning an animal relative to the measurement device is challenging, especially in view of the above-noted tendency of animals to frequently change their body position or at least their head position.

Moreover, the differences in facial structure between humans and animals also cause such eye health measurement devices to be difficult to use on animals. For example, many dogs have a nose that extends significantly farther than a human nose. As a result positioning the eye of the dog at the proper distance and angles relative to the measurement device can be problematic.

Therefore, there is a need for devices and methods for positioning one or more eyes of an animal by securing the animal's head and eyes in position while obtaining objective measurements associated with eye health.

SUMMARY OF THE INVENTION

It is, therefore, an object of the invention to provide devices suitable for seeming the head and eyes of an animal in position while obtaining objective measurements associated with eye health.

It is another object of the invention to provide methods for securing an animal's head and eyes in position while obtaining objective measurements associated with eye health.

It is yet another object of the invention to provide methods for promoting the health or wellness of an animal by obtaining objective measurements associated with eye health.

It is still another object of the invention to provide kits having devices and instructions for securing the head and eyes of an animal in position while obtaining objective measurements associated with eye health.

It is another object of the invention to provide packages and indicia describing the contents of the package including the device for securing the head and therefore the eyes of an animal in position.

One or more of these or other objects are achieved by providing a positioning device including a rest for receiving a portion of an animal's head and therefore securing the animal's head and eyes in position while obtaining objective measurements associated with eye health. The positioning device includes a pole configured to enable the rest to pivot about a first axis of rotation and rotate about a second axis of rotation perpendicular to the first axis of rotation. The positioning device can include a tilt adjustment member for pivoting the test about the first axis of rotation and a clocking adjustment member for rotating the rest about the second axis of rotation. The positioning device can include a height adjustment member for moving the rest up and down the second axis of rotation.

Other and further objects, features, and advantages of the present invention will be readily apparent to those skilled in the art.

DETAILED DESCRIPTION OF THE INVENTION

Definitions

Figure 1:
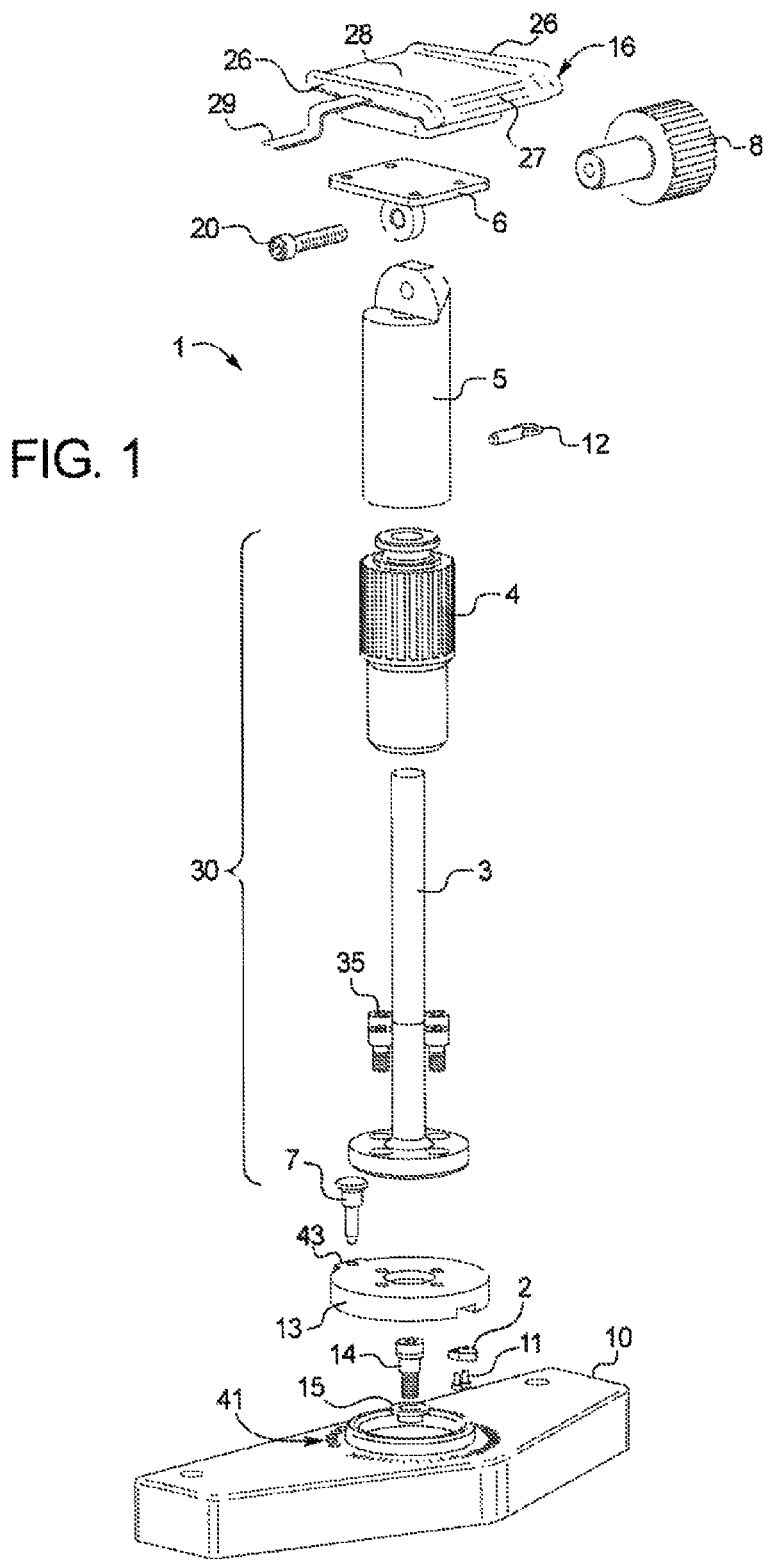
FIG. 1 shows an exploded perspective view of a positioning device for securing an animal's head in position in an embodiment of the invention.

The term "securing an animal's eyes" and its equivalents means that the device of the invention secures an animal's head and eye socket in a manner that prevents the animal's eyeball from moving substantially when compared to the device and any equipment used for obtaining objective measurements associated with eye health.

The term "in position" means little or no movement of an animal's head, eye socket, and eyes while measurements associated with eye health are taken by an observer.

The term "animal" means any animal that could benefit from securing the eyes in place during examination, including avian, bovine, canine, equine, feline, hircine, lupine, murine, ovine, or porcine animals, and preferably a domesticated animal, and more preferably a companion animal.

The term "companion animal" means domesticated animals such as dogs, cats, birds, rabbits, guinea pigs, ferrets, hamsters, mice, gerbils, pleasure horses, cows, goats, sheep, donkeys, pigs, and more exotic species kept by humans for company, amusement, psychological support, education, physical assistance, extrovert display, and all of the other functions that humans desire or need to share with animals of other species. The term "companion animal" also means a dog or a cat.

As used herein, the singular form of a word includes the plural, and vice versa, unless the context clearly dictates otherwise. Thus, the references "a", "an", and "the" are generally inclusive of the plurals of the respective terms. For example, reference to "securing an animal's eye" includes securing an animal's eyes, and vice versa. Also, the words "comprise", "comprises", and "comprising" are to be interpreted inclusively rather than exclusively. Likewise the terms "include", "including" and "or" should all be construed to be inclusive, unless such a construction is clearly prohibited from the context.

The terms "comprising" or "including" are intended to include embodiments encompassed by the terms "consisting essentially of" and "consisting of". Similarly, the term "consisting essentially of" is intended to include embodiments encompassed by the term "consisting of".

The methods and compositions and other advances disclosed here are not limited to particular methodology, protocols, and reagents described herein because, as the skilled artisan will appreciate, they may vary. Further, the terminology used herein is for describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the fields(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant; material, or prior art. The right to challenge the accuracy and pertinence of any assertion of such patents, patent applications, publications, and other references as relevant, material, or prior art is specifically reserved.

The Invention

Figure 2:
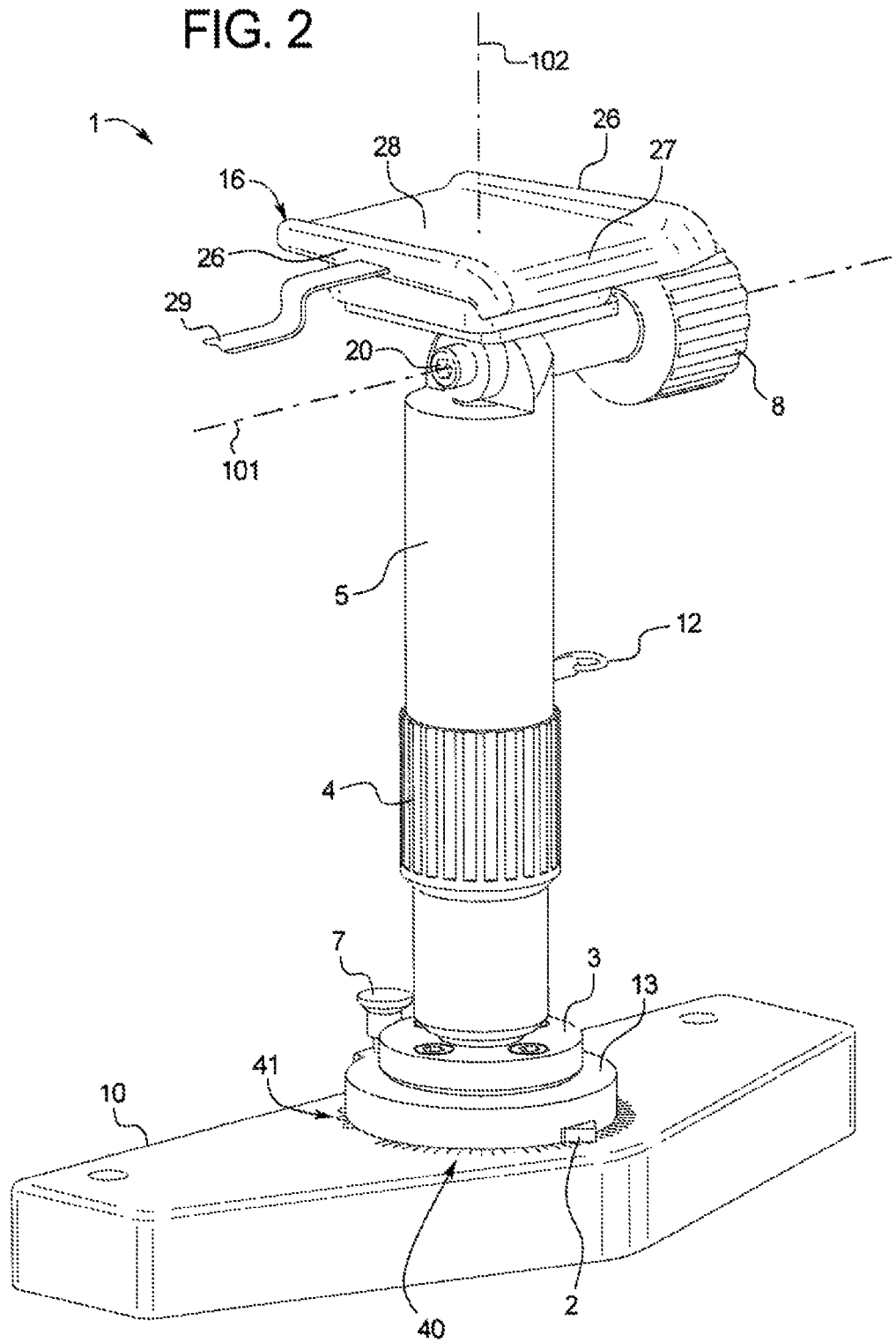
FIG. 2 shows a perspective view of the positioning device in an embodiment of foe invention.
Figure 3:
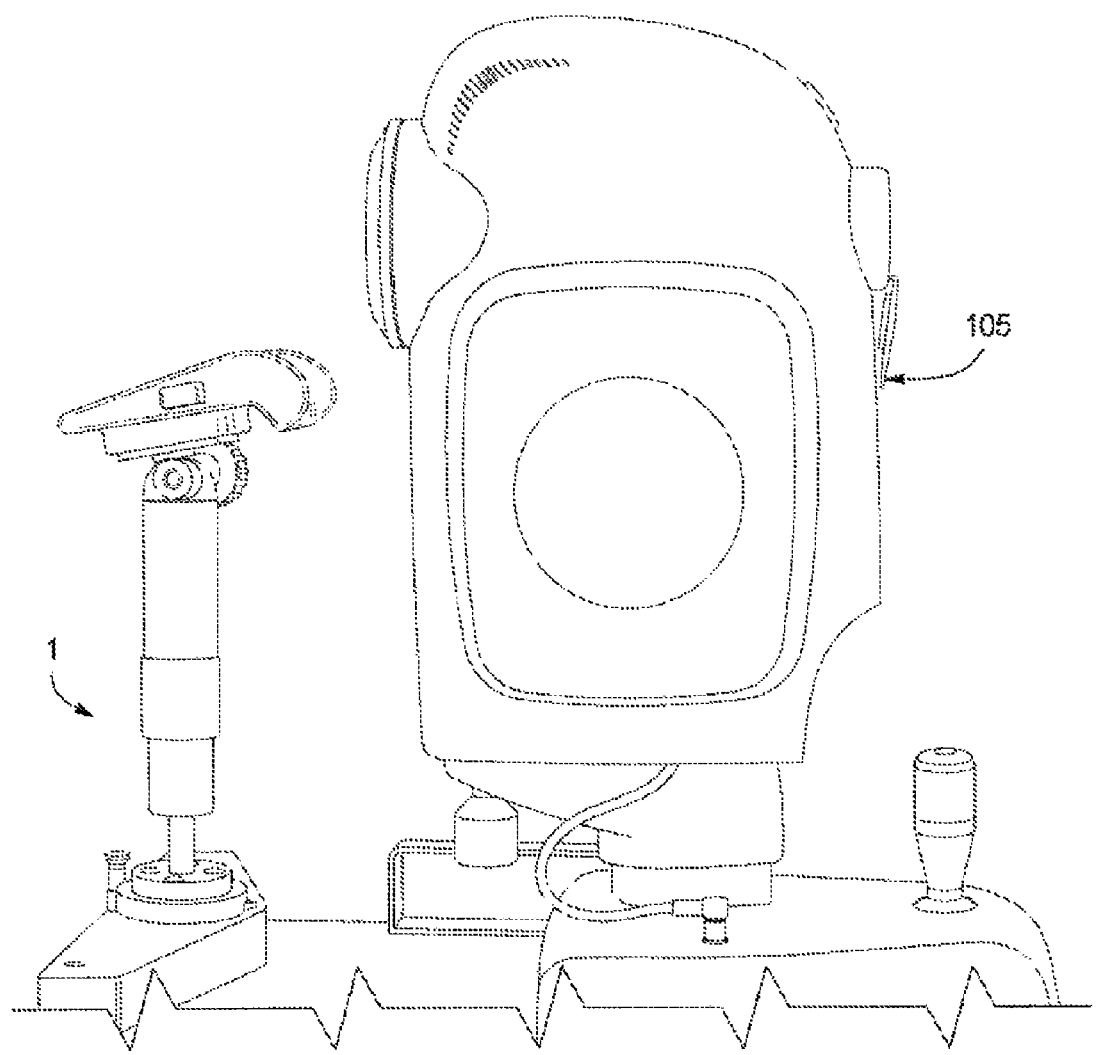
FIG. 3 shows a side perspective view of the positioning device connected to an eye health measurement device in an embodiment of the invention.

In one aspect, as shown in FIGS. 1-3, the invention provides a positioning device 1 including a rest 16 having side flanges 26 extending at least partially upward therefrom. The rest 16 can have a substantially planar portion 28 located between the side flanges 26 and can also have a neck flange 27 extending outward and/or downward from the substantially planar portion 28. The rest 16 receives a portion of an animal's head. For example, one of the side flanges 26 can contact at least a portion of a side of the animal's head, the other side flange 26 can contact at least a portion of the other side of the animal's head, the neck flange 27 can contact at least a portion of the animal's neck, and the substantially planar portion 28 can contact at least a portion of the underside of the animal's head.

The device secures the eyes of an animal in position such that objective measurements associated with eye health can be obtained. The animal's eye is secured in position by securing the anima's head in a manner that prevents any substantial movement of the animal's eye (eye socket) in relation to the device.

In an embodiment, the positioning device 1 includes a strap 29 that can extend from at least one side of the rest 16 and can be configured to reversibly connect to at least one other side of the rest 16. The length of the strap 29 can be adjustable. For example, the length of the strap 29 can be adjusted to accommodate the animal's head received by the rest 16 and secure the animal's head and/or eye in position relative to the rest 16. Depending on the facial structure of the animal, the strap 29 can secure the animal's head and/or the animal's eye in position relative to the rest 16 by at least partially encircling the nose of the animal, in an embodiment, the strap 29, the substantially planar portion 28, the neck flange 27 and/or the interior surfaces of the side flanges 26 are padded to reduce or prevent discomfort for the animal.

As shown in FIG. 2, the positioning device 1 includes a pole 5 configured to enable the rest 16 to pivot about a first axis of rotation 101 and rotate about a second axis of rotation 102 perpendicular to the first axis of rotation 101. The pole 5 can be co-linear with the second axis of rotation 102 such that the pole 5 is positioned on the second axis of rotation 102. Rotation of the pole 5 and/or the rest 16 about the second, axis of rotation 102 can rotate the first axis of rotation 101 in the horizontal plane. As used herein, the term "horizontal plane" is the horizontal plane perpendicular to the second axis of rotation 102 and passing through the first axis of rotation 101, and the term "clocking" means the angle in the horizontal plane.

Referring again to FIG. 1 and FIG. 2, the positioning device 1 can include a device base 10 that can have a fixed position such that pivoting the rest 16 about the first axis of rotation 101 changes the angle of the rest 16 relative to the device base 10 in the vertical plane. For example, pivoting the rest 16 about the first axis of rotation 101 decreases the distance from one end of the rest 16 to the device base 10 and increases the distance from the opposite end of the rest 16 to the device base 10. As used herein, the term "vertical plane" is the vertical plane perpendicular to the first axis of rotation 101 and passing through the second axis of rotation 102, and the term "tilt" means the angle in the vertical plane.

Pivoting the rest 16 about the first axis of rotation 101 changes the tilt of the rest 16, and changing the tilt of the rest 16 can position the animal's head and/or the animal's eye at a desired angle in the vertical plane. Rotating the rest 16 about the second axis of rotation 102 changes the clocking of the rest 16, and changing the clocking of the rest 16 can position the animal's head and/or the animal's eye at a desired angle in the horizontal plane.

In an embodiment, the positioning device 1 includes an attachment member 6 to which the rest 16 can be reversibly connected and disconnected. The positioning device 1 can include a tilt adjustment member 8 that can enable the rest 16 and/or the attachment member 6 to move to a desired tilt. For example, the tilt adjustment member 8 can be a first knob that can be rotatable in one direction to enable the rest 16 to be pivoted and can be rotatable in an opposite direction to prevent the rest 16 from being pivoted.

In an embodiment, the positioning device 1 includes a retaining screw 20 that connects the rest 16 and/or the attachment member 6 to the pole 5. For example, the retaining screw 20 can extend through the attachment member 6 and the pole 5 to the opposite side of the pole 5 to insert into the tilt adjustment member 8.

The tilt adjustment member 8 can be rotatable in one direction to enable the rest 16 to be pivoted and can be rotatable in an opposite direction to prevent the rest 16 from being pivoted. For example, the tilt adjustment member 8 can be rotated in one direction to loosen the connection between the tilt adjustment member 8 and the retaining screw 20, and the loosened connection can enable the rest 16 to pivot to a desired tilt. Then rotation of the tilt adjustment member 8 in an opposite direction can tighten the connection between the tilt adjustment member 8 and the retaining screw 20, and the tightened connection can maintain the rest 16 at the desired tilt.

When at least a portion of an animal's head is received by the rest 16, the tilt adjustment member 8 can be rotated in the first direction to enable the rest 16 to pivot the animal's head, and/or the animal's eye to a desired tilt. Then the tilt adjustment member 8 can be rotated in the second direction to prevent the rest 16 from being pivoted such that the rest 16 maintains the animal's head and/or the animal's eye at the desired tilt.

The positioning device 1 can include a height adjustment member 30 for moving the rest 16 up and down the second axis of rotation 102. The pole 5 can connect to the height adjustment member 30. In an embodiment, the height adjustment member 30 includes a second knob 4 to which the pole 5 connects. The second knob 4 can be co-linear with the second axis of rotation 102 and/or the pole 5 such that the second knob 4 is positioned on the second axis of rotation 102.

In an embodiment, the height adjustment member 30 includes a stem 3 positioned on the second axis of rotation 102. The stem 3 can connect to the second knob 4 and/or the pole 5 such that rotation of the stem 3 rotates the pole 5 and/or the rest 16 relative to the second axis of rotation. In an embodiment, the pole 5 and/or the second knob 4 include threads complementary to threads on the stem 3, and the complementary threads enable the second knob 4 to move along the second axis of rotation 102 if the second knob 4 is rotated. For example, rotation of the second knob 4 in one direction can move the second knob 4 up the second axis of rotation 102, and rotation of the second knob 4 in an opposite direction can move the second knob 4 down the second axis of rotation 102.

Moving the second knob 4 up the second axis of rotation 102 moves the pole 5 and/or the rest 16 up the second axis of rotation 102 to increase the distance between the rest 16 and the device base 10. Moving the second knob 4 down the second axis of rotation 102 moves the pole 5 and/or the rest 16 down the second axis of to decrease the distance between the rest 16 and the device base 10. As a result, the height adjustment member 30 the second knob 4 and/or the stem 3 can adjust a height of the rest 16, and adjusting the height of the rest 16 can adjust the height of the animal's head received by the rest 16. For example, the second knob 4 can be rotated to move the animal's head and/or the animal's eye to a desired height.

The positioning device 1 can include a release pin 12 that can insert at least partially through the pole 5, the second knob 4 and/or the stem 3 to prevent the pole 5 from moving up the second axis of rotation 102. For example, the release pin 12 can be inserted to prevent the pole 5 and the rest 16 from being pulled up and off of the second knob 4 if there is any upward force on these components either from the animal or human operator.

In an embodiment, the positioning device 1 includes a clocking adjustment member 13 to which the stem 3 connects. For example, the positioning device 1 can include one or more screws 35 inserted through the stem 3 into the clocking adjustment member 13 to connect the stem 3 to the clocking adjustment member 13. The clocking adjustment member 13 can be rotatably connected to the device base 10. For example, the positioning device 1 can include a shoulder screw 14 and/or a shoulder washer 15 that connect the clocking adjustment member 13 to the device base 10. The shoulder screw 14 and the shoulder washer 15 can be co-linear with the second axis of rotation 102 to enable the clocking adjustment member 13 and/or the stem 3 to rotate on the second axis of rotation 102. In an embodiment, the clocking adjustment member 13, the stem 3, the pole 5 and the rest 16 are arranged to rotate together such that rotation of one of these components rotates the remainder of these components. For example, subjecting the clocking adjustment member 13 to a specific amount of rotation subjects the stem 3, the pole 5 and the rest 16 to the same amount of rotation.

The positioning device 1 can include an angle indicator 2 extending from the clocking adjustment member 13. For example, the angle indicator 2 can be connected to the clocking adjustment member 13 by screws 11. Alternatively or additionally, the angle indicator 2 can be integral with the clocking adjustment member 13. The device base 10 can have indicia 40 printed and/or formed thereon, and the angle indicator 2 can align with one of the indicia 40 on the device, base 10 to identify the clocking of the rest 16.

The positioning device 1 can include a spring lock pin 7, and the device base 10 can include holes 41 having a shape corresponding to the spring lock pin 7. The clocking adjustment member 13 can have an aperture 43 through which the spring lock pin 7 can at least partially insert. For example, the spring lock pin 7 can at least partially insert through the aperture 43 in the clocking adjustment member 13 into one of the holes 41 to prevent the clocking adjustment member 13, the stem 3, the pole 5 and/or the rest 16 from rotating on the second axis of rotation 102. To rotate the rest 16, the spring lock pin 7 can be removed from the hole 41 in which the spring lock pin 7 was inserted, and then the clocking adjustment member 13, the stem 3, the pole 5 and/or the rest 16 can be rotated on the second axis of rotation 102 to a desired clocking. Then the spring lock pin 7 can at least partially insert into another one of the holes 41 to prevent the clocking adjustment member 13, the stem 3, the pole 5 and/or the rest 16 from rotating. Insertion of the spring lock pin 7 can maintain the position of the rest 16, the animal's head and/or the animal's eye at the desired clocking.

In an embodiment, the holes 41 are positioned at ten degree increments of rotation about the second axis of rotation 102. In an embodiment, the holes 41 are arranged such that the rest 16 can rotate one-hundred twenty degrees. However, other embodiments can have any number of holes 41 and can have any maximum amount of rotation, and the positioning device 1 is not limited to a specific number of the holes 41 or a specific maximum amount of rotation.

The positioning device 1 can be made from any suitable material such as a polymer, a plastic and/or another synthetic material. For example, the positioning device 1 can be made from a polyethylene material such as linear low density polyethylene, polypropylene, polyethylene terephthalate, and/or the like. Alternatively or additionally, the positioning device 1 can be manufactured front non-plastic materials including, but not limited to, glass; ceramic; cardboard; metal, such as aluminum or stainless steel; styrofoam; and/or the like.

In an aspect shown in FIG. 3, the device base 10 can attach to an eye health measurement device 105. In an embodiment, the positioning device 10 can replace a human chin rest assembly. For example, a human chin rest assembly connected to the eye health measurement device 105 by connecting bolts (not shown) can be removed by loosening the connecting bolts, and then the positioning device 1 can be connected to the eye health measurement device 105 by inserting the connecting bolts through the device base 10.

In an embodiment, the eye health measurement device 105 is an aberrometer, a topographer or a combination thereof. For example, the eye health measurement device 105 can perform ray tracing by transmitting parallel light beams through the animal's pupil and determining where the light beams land on the animal's retina. The landing locations can be used to measure the overall eye health and can be used to create a graphical display that can be analyzed to determine visual function. However, the eye health measurement device 105 can be any device that obtains objective measurements associated with eye health, and the eye health measurement device 105 is not limited to a specific embodiment.

The rest 16 receives at least a portion of an animal's head, positions the animal's head and secures the animal's eye in position relative to the eye health measurement device 105. For example, the side flanges 26 can contact at least a portion of the sides of the animal's head, and the neck flange 27 can contact at least a portion of the animal's neck to position the animal's head and secure the animal's eye in position relative to the eye health measurement device 105. The positioning device 1 can secure the animal's head and/or the animal's eye in position at a desired position relative to the eye health measurement device 105. For example, the positioning device 1 can secure the animal's head and/or the animal's eye in position at a desired clocking, a desired tilt and/or a desired height.

In an embodiment, in which eye health measurements of a dog are obtained, the rest 16 receives at least a portion of a dog's head, positions the dog's head and secures the dog's eye in position relative to the eye health measurement device 105. For example, the side flanges 26 can contact at least a portion of the sides of the dog's head, and the neck flange 27 can contact at least a portion of the dog's neck to position the dog's head and secure the dog's eye in position relative to an eye health measurement device 105. The positioning device 1 can secure the dog's head and/or the dog's eye in position at a desired tilt, a desired clocking and/or a desired height relative to the eye health measurement device 105. If the dog has a nose that extends a distance outward relative to the clog's eye, the positioning device 1 can position the dog's head such that the dog's nose does not block positioning of the eye health measurement device 105 or transmission of light from the eye health measurement device 105 to the dog's eye.

Figure 4:
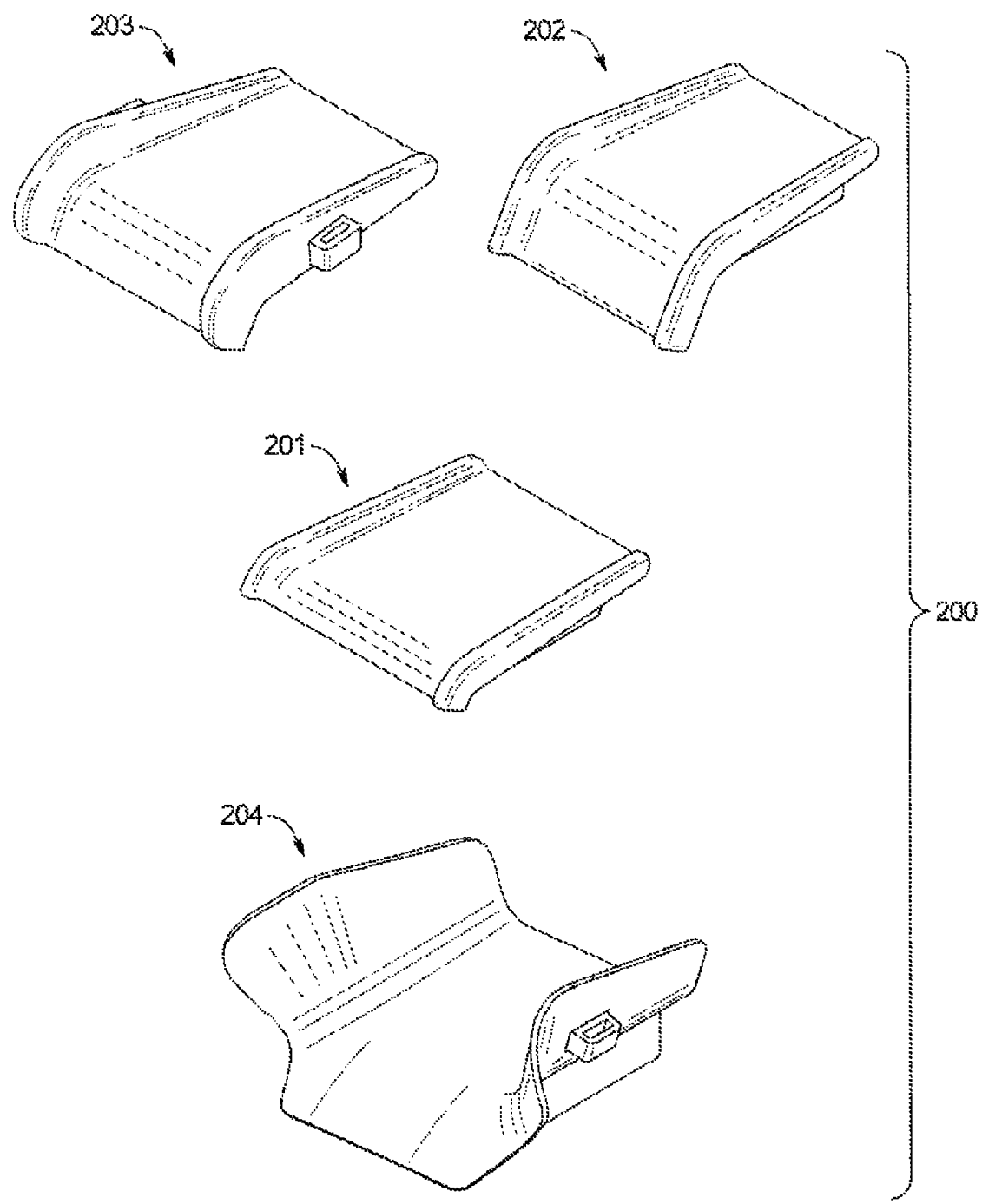
FIG. 4 shows a plurality of rests that can be used with the positioning device in an embodiment of the invention.

In an aspect shown in FIG. 4, the rest 16 can be one of a plurality of rests 200 that have different sizes relative to each other. For example, the plurality of rests 200 can include a first rest 201 having a shorter neck flange relative to another one of the plurality of rests 200. The first rest 201 can be suitable for an animal with a shorter neck than the animal for which the other rest is used. As another example, the plurality of rests 200 can include a second rest 202 having a longer neck flange relative to another one of the plurality of rests 200. The second rest 202 can be suitable for an animal with a longer neck than the animal, for which the other rest is used. As yet another example, the plurality of rests 200 can include a third rest 203 having side flanges with a larger height relative to another one of the plurality of rests 200. The third rest 203 can be suitable for an animal with a larger head relative to the animal for which the other rest is used. Moreover, a fourth rest 204 can have side flanges that extend outward in addition to upward and can have a longer neck flange relative to another one of the plurality of rests 200. The fourth rest 204 can be suitable for an animal with a larger bead relative to the animal for which the other rest is used.

The first rest 201, the second rest 202, the third rest 203 and the fourth rest 204 are merely examples, and the plurality of rests 200 can include any combination of rests. Each of the plurality of rests 200 can have different dimensions with respect to the substantially planar surface, the side flanges, the neck flange and/or other components of the rest.

The plurality of rests 200 can be used with the positioning device 1 to secure the eye of an animal in position while obtaining objective measurements associated with eye health. One of the plurality of rests 200 can be selected based on the features of the animal and then attached to the pole 5. For example, a first rest can be selected from the plurality of rests 200 and can reversibly connect to from the attachment member 6. The first rest can receive a portion of the animal's head, and the pole 5 can be configured to enable the first rest to rotate about at least one axis of rotation. The attachment member 6 can be configured to pivot relative to the pole 5 and mount the first rest on the pole 5.

In an embodiment, each of the plurality of rests 200 has a different size relative to each other. The side flanges of one of the plurality of rests 200 can have a different height relative to the side flange of at least one other one of the plurality of rests 200. The neck flange of one of the plurality of rests 200 can have a different length relative to the neck flange of at least one other one of the plurality of rests 200.

The first rest can be replaced by a second rest of the plurality of rests 200. For example, the second rest can be selected for use with an animal having different features relative to the animal with which the first rest was used, the first rest can be disconnected from the attachment member, and then the second rest can be connected to the attachment member. The second rest can have at least one differently sized component relative to the first rest.

In yet another aspect, the invention provides a method for securing an animal's eye in position while obtaining objective measurements associated with eye health. The method includes positioning at least a portion of the animal's head in a device comprising a rest, and adjusting an angle of the animal's head in at least one of a vertical plane or a horizontal plane relative to a measurement device by rotating the rest to obtain the objective measurements. Adjusting the angle of the animal's head in the vertical plane relative to the measurement device can position the animal's eye at a desired tilt, and adjusting the angle of the animal's head in the horizontal plane relative to the measurement device can position the animal's eye at a desired clocking.

The method can include adjusting a height of the animal's head relative to the measurement device by moving the rest. In an embodiment, positioning at least a portion of the animal's head includes positioning at least a portion of the animal's neck. The method can include securing the animal's head to the rest with a strap. In an embodiment, the measurement device can be one of an aberrometer, a topographer or a combination thereof. For example, the measurement device can perform ray tracing by transmitting parallel light beams through the animal's pupil and determining where the light beams land on the animal's retina. The landing locations can be used to measure the overall eye health and can be used to create a graphical display that can be analyzed to determine visual function. However, the measurement device can be any device that obtains objective measurements associated with eye health.

In an alternative aspect, the invention provides a method, for obtaining objective measurements associated with eye health. The method includes placing an animal's head on a positioning device comprising a rest that pivots about a first axis of rotation and rotates about a second axis of rotation perpendicular to the first axis of rotation; and measuring one or more parameters associated with an eye of the animal.

In another alternative aspect, the invention provides a method for promoting the health or wellness of an annual. The method includes placing an animal's head on a positioning device; adjusting at least, one of an angle of the animal's head in the vertical plane, an angle of the animal's head in the horizontal plane, or a height of the animal's head using the positioning device; and obtaining objective measurements associated with eye health of the animal. The method can include providing a health protocol for the animal to follow based on the objective measurements.

In yet another alternative aspect, the invention provides a means for communicating information about or instructions for one or more of (1) a positioning device comprising a rest configured to pivot about a first axis of rotation and rotate about a second axis of rotation perpendicular to the first axis of rotation; (2) using the positioning device to obtain objective eye health measurements; (3) cleaning the positioning device; (4) an eye health measurement device to be used with the positioning device; (5) instructions for securing an animal's eye for obtaining objective measurements associated with eye health; (6) instructions for obtaining objective measurements associated with eye health using the positioning device; or (7) instructions for promoting the health or wellness of an animal using the positioning device.

The communication means can be a document, digital storage media, optical storage media, audio presentation, or visual display containing the information or instructions. More specifically, the means can be a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, or any combination thereof.

Useful information includes contact information for consumers to use if they have a question about the invention and its use. The communication means is useful for instruction on the benefits of using the present invention and communicating the approved methods for using the invention to secure securing an animal's eye in position while obtaining objective measurements associated with eye health.

In an alternative aspect, the invention provides kits useful for obtaining objective measurements associated with eye health using the devices of the invention. The kits include in separate containers in a single package or in separate containers in a virtual package, as appropriate for the kit component, a positioning device comprising a rest that pivots about a first axis of rotation and rotates about a second axis of rotation perpendicular to the first axis of rotation, and at least one of (1) instructions on how to use the positioning device to secure the animal's eye in position; (2) instructions on how to use the positioning device to obtain objective measurements associated with eye health; (3) instructions on how to use an eye health measurement device that obtains the objective measurements with the positioning device; (4) Instructions on how to clean the positioning device; (5) a toy that can be used to draw the animal to the positioning device; (6) a food product that can be used to draw the animal to the positioning device; (7) nutritional information about food products that promote eye health; or (8) one or more secondary rests that can be interchangeable with the rest.

When the kits comprise a virtual package, the kits are limited to instructions in a virtual environment in combination with one or more physical kit components. The kits can contain the kit components in any of various combinations. In one embodiment, the kit contains a positioning device as described herein. In another embodiment, an eye health measurement device can be sold with the kit or sold separately from the kit, for example, as a virtual kit.

The kits can encompass one or more kit components that are ordered and shipped separately to the consumer, for example, such as an order on the internet or by phone tor a positioning device and an eye health measurement device, wherein the two articles are shipped from separate locations to the consumer's address.

In another aspect, the invention provides a package including indicia describing a positioning device comprising a rest to be used to secure an animal's eye for obtaining objective measurements associated with eye health. The indicia can be in the form of words, symbols, pictures, photographs, figures or combinations thereof to show details or examples of the positioning device described herein. The package can further contain a positioning device comprising a rest that receives a portion of an animal's head, pivots about a first axis of rotation, and rotates about a second axis of rotation perpendicular to the first axis of rotation.

In an embodiment, the package includes one or more handles suitable for handling and transporting the package. The package can include one or more windows for viewing the positioning device or any parts thereof. The package can include a label affixed to the package containing a word or words, picture, design, acronym, slogan, phrase, or combination thereof, that indicates that the package contains a positioning device for securing an animal's eye for obtaining objective measurements associated with eye health.

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims the invention may be practiced otherwise than as specifically described.

What is claimed is:

1. A device (1) suitable for securing an animal's eye in position while obtaining objective measurements associated with eye health comprising:
   a rest (16) for receiving a portion of the animal's head;
   a clocking adjustment member (13) connected to the rest (16); and
   a tilt adjustment member (8) connected to the rest (16);
   wherein the tilt adjustment member (8) comprises a knob (8) rotatable in a first direction to enable the rest (16) to pivot to a desired tilt and rotatable in a second direction opposite to the first direction to prevent the rest (16) from pivoting from the desired tilt.

2. The device (1) of claim 1 wherein the rest (16) is at least partially planar.

3. The device (1) of claim 1 wherein the rest (16) comprises side flanges (26) that extend at least partially upward from opposite sides of the rest (16).

4. The device (1) of claim 1 comprising an adjustable strap (29) extending from at least one side of the rest (16).

5. The device (1) of claim 1 wherein the rest (16) comprises a neck flange (27) that extends downward and outward from one side of the rest (16).

6. The device (1) of claim 1 comprising a height adjustment member (30).

7. The device (1) of claim 6 wherein the height adjustment member (30) comprises a stem (3) having threads configured to enable the rest (16) to move up and down.

8. The device (1) of claim 6 wherein the height adjustment member (30) comprises a knob (4) rotatable in a first direction to move the rest (16) up the second axis of rotation (102) and rotatable in a second direction opposite to the first direction to move the rest (16) down the second axis of rotation (102).

9. The device (1) of claim 1 comprising a base (10) connected to the pole (5), the base (10) attachable to a measurement device (105) that obtains the objective measurements.

10. The device (1) of claim 1 comprising a pole (5) to which the rest (16), the clocking adjustment member (13) and the tilt adjustment member (8) are connected.

11. A device (1) suitable for securing an animal's eye in position while obtaining objective measurements associated with eye health comprising:
   a rest (16) for receiving a portion of the animal's head;
   a pole (5) configured to enable the rest (16) to rotate about at least one axis of rotation (101,102); and
   an attachment member (6) configured to pivot relative to the pole (5) and mount the rest (16) on the pole (5), the rest (16) configured to reversibly connect to and disconnect from the attachment member (6).

12. A method for securing an animal's eye in position while obtaining objective measurements associated with eye health comprising:
   positioning at least a portion of the animal's head in the device (1) of claim 1 or 11; and
   adjusting an angle of the animal's head in at least one of a vertical plane or a horizontal plane relative to a measurement device (105) by rotating the rest (16) to obtain the objective measurements.

13. The method of claim 12 further comprising adjusting a height of the animal's head relative to the measurement device (105) by moving the rest (16).

14. The method of claim 12 wherein positioning at least a portion of the animal's head comprises positioning at least a portion of the animal's neck using the rest (16).

15. The method of claim 12 further comprising securing the animal's head to the rest (16) with a strap (29).

16. The method of claim 12 wherein the measurement device (105) is selected from the group consisting of an aberrometer, a topographer and a combination thereof.

17. The device (1) of claim 11 wherein the rest (16) is one of a plurality of rests (200) that have different sizes relative to each other.

18. The device (1) of claim 11 wherein the rest (16) is one of a plurality of rests (200) and has side flanges (26) extending at least partially upward that have a different height relative to the side flanges (26) of at least one other rest (16) of the plurality of rests (200).

19. The device (1) of claim 11 wherein the rest (16) is one of a plurality of rests (200) and has a neck flange (27) extending downward and outward that has a different length relative to the neck flange (27) of at least one other rest (16) of the plurality of rests (200).

20. A method for obtaining objective measurements associated with eye health comprising:
   placing an animal's head on the device (1) of claim 1 or 11; and
   measuring one or more parameters associated with an eye of the animal.

\* \* \* \* \*